(12) United States Patent
Yenofsky et al.

(10) Patent No.: US 6,710,228 B1
(45) Date of Patent: *Mar. 23, 2004

(54) COTTON CELLS, PLANTS, AND SEEDS GENETICALLY ENGINEERED TO EXPRESS INSECTICIDAL AND FUNGICIDAL CHITIN BINDING PROTEINS (LECTINS)

(75) Inventors: Richard L. Yenofsky, Arcadia, CA (US); Miriam Fine, Arcadia, CA (US); Thirumale S. Rangan, Lubbock, TX (US); David M. Anderson, Placentia, CA (US)

(73) Assignee: Mycogen Corporation, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/322,640

(22) Filed: May 28, 1999

Related U.S. Application Data

(60) Provisional application No. 60/087,219, filed on May 29, 1998.

(51) Int. Cl.⁷ .................. C12N 15/09; C12N 15/29; C12N 15/82; A01H 5/00; A01H 5/10
(52) U.S. Cl. .................. 800/279; 800/314; 800/278; 800/298; 800/295; 800/301; 800/302; 435/69.1; 435/468; 435/419; 536/23.1; 536/23.6
(58) Field of Search .................. 800/279, 278, 800/295, 298, 301, 302, 314; 536/23.1, 23.6; 435/69.1, 468, 469, 419, 427, 430

(56) References Cited

U.S. PATENT DOCUMENTS

| | | | |
|---|---|---|---|
| 5,187,262 A | 2/1993 | Raikhel et al. | 530/370 |
| 5,276,269 A | * 1/1994 | Raikhel et al. | 800/205 |
| 5,399,668 A | * 3/1995 | Raikhel et al. | 530/350 |
| 5,436,392 A | 7/1995 | Thomas et al. | |
| 5,994,625 A | * 11/1999 | Melchers et al. | 800/279 |
| 6,006,470 A | * 12/1999 | Geoghegan et al. | 47/58.1 |

FOREIGN PATENT DOCUMENTS

| | | | |
|---|---|---|---|
| EP | 0351924 | | 1/1990 |
| EP | 0502718 | | 9/1992 |
| WO | 8905344 | | 6/1989 |
| WO | WO 92/15690 | * | 9/1992 |
| WO | 9408009 | | 4/1994 |
| WO | 9411511 | | 5/1994 |
| WO | 9526634 | | 10/1995 |

OTHER PUBLICATIONS

Linthorst et al. The Plant Cell, vol. 1, pp. 285–291, Mar. 1989.*

Dandekar et al. Plant Science, Vol 96, pp. 151–162, Mar. 1989.*

Wilkins, T. A. et al. Role of Propeptide Glycan in Post–Translational Processing and Transport of Barley Lectin to Vacuoles in Transgenic Tobacco, *The Plant Cell*, vol. 2, 301–313 1990.

Murdock, L. L. et al. "Biological Effects of Plant Lectins on the Cowpea Weevil," *Phytochemistry*, vol. 29 No. 1, pp 85–89 (1990).

Rajasekaran, K. et al. "Herbicide–resistant Acala and Coker cottons transformed with a native gene encoding mutant forms of acetohydroxyacid synthase," *Molecular Breeding* 2:307–319 (1996).

Lerner, D. R. et al. "The gene for stinging nettle lectin (*Urtica dioica* agglutinin) encodes both a lectin and a chitinase," *J. Biological Chemistry* 267: 22694 (1992).

Lee, H. et al., "Co– and Post–translational Processing of the Hevein Preproprotein of Latex of the Rubber Tree (*Hevea Brasiliensis*)," *J. Biological Chemistry* 15944–15948 (1991).

Broekaert, W., et al. Wound–induced accumulation of mRNA containing a hevein sequence in laticifers of rubber tree (*Hevea brasiliensis*), Proc. Natl. Acad. Sci, USA 87: 7633–7637 (1990).

Anderson, D., et al., "Chlorophyll a/b–Binding Protein Gene Expression in Cotton," *Plant Physiol.* 102: 1047–1048 (1993).

Umbeck, P., et al. Genetically Transformed Cotton (*Gossypium Hirsutum* L.) Plants, *Bio/Technology* 5:263–266 (1987).

Blake, M. S., et al. "A Rapid, Sensitive Method for Detection of Alkaline Phosphatase–Conjugated Anti–antibody on Western Blots," *Analytical Biochemistry* 136:175–179 (1984).

Singh, M. et al., "White's Standard Nutrient Solutions," *Ann. Bot.* 47:133–139 (1981).

Raikhel, N. V., et al. "Characterization of a wheat germ agglutinin–like lectin from adult wheat plants," *Planta* 162:55–61 (1984).

Lerner, D. R., et al. "Cloning and characterization of Root–Specific Barley Lectin," *Plant Physiol.* 91:124–129 (1989).

Firoozabady, E., et al. "Transformation of cotton (*Gossypium hirsutum* L.) By Agrobacterium tumefaciens and regeneration of transgenic plants," *Plant Molecular Biology* 10: 105–116 (1987).

(List continued on next page.)

Primary Examiner—Elizabeth F. McElwain
Assistant Examiner—Medina A. Ibrahim
(74) Attorney, Agent, or Firm—Saliwanchik, Lloyd & Saliwanchik

(57) ABSTRACT

Chimeric genes encoding lectins exhibiting pesticidal activity (for example, insecticidal and/or fungicidal activity) are disclosed which can be used to transform cotton to yield cotton cells, plants, and seeds in which the chimeric genes are expressed. Such transformed cotton cells are pesticidal when ingested by cotton pests.

21 Claims, 4 Drawing Sheets

OTHER PUBLICATIONS

Murashige, T. and Skoog, F. A Revised Medium for Rapid Growth and Bio Assays with Tobacco Tissue Cultures (1962) *Physiol. Plant.* 15:473497.

Schroeder, M. R. and Raikhel, N. V. (1992) *Protein Expr. Purif.* 3:508–511.

Rajguru, S. et al. "Assessment of Resistance of Cotton Transformed with Lectin Genes to Tobacco Budworm" 1998 Proceedings Beltwide Cotton Conferences, San Diego, California, USA Jan. 5–9, 1998. vol. I, (1998) PP490–491, Jan. 1998.

Rajguru, S., et al. "Assessment of resistance of cotton transformed with lectin genes to tobacco budworm" *Special Report*—Arkansas Agricultural Experiment Station 1998 No. 188 pp. 95–98 1998.

Willem F. Broekaert et al. "A Chitin–Binding Lectin from Stinging Nettle Rhizomes with Antifungal Properties" *Science*, vol. 245, Sep. 8, 1989 pp. 1100–1102.

Paul R. Burrows et al. Plant–Derived Enzyme Inhibitors and Lectins for Resistance against Plant–Parasitic Nematodes in Transgenic Crops, *Pestic. Sci.* Feb. 1998 vol. 52, No. 2, pp 176–183.

W. J. Peumans et al. "Lectins as Plant Defense Proteins" Plant Physiol. 1995 109:347–352.

Zhou, G., et al. "Introduction of Exogenous DNA into Cotton Embryos" *Methods In Enzymology*, vol. 101, pp 433–481.

Chemical Abstracts, vol. 123, No. 21 1995, Abstract No. 281213 Lee, H. I. et al. "Prohevein is poorly processed but shows enhanced resistance to a chitin–binding fungus in transgenic tomato plants" Abstract & *Braz. J. Med. Biol. Res.* vol. 28, No. 7 1995, pp 743–750.

Gatehouse, A. M. R. et al. "Identifying Proteins with Insecticidal Activity: Use of Encoding Genes to Produce Insect–Resistant Transgenic Crops" Pestic. Sci., vol. 52, No. 2, 1998, pp. 165–175.

* cited by examiner

```
  1 CAGAAAACAA GAAGGATGAA GATGATGAGC ACCAGGGCCC TCGCTCTCGG CGCGGCCGCC
 61 GTCCTCGCCT TCGCGGCGGC GACCGCGCAC GCCCAGAGGT GCGGCGAGCA GGCCAGCAAC
121 ATGGAGTGCC CCAACAACCT CTGCTGCAGC CAGTACGGGT ACTACGGCAT GGGCGGCGAC
181 TACTGCGGCA AGGGCTGCCA GAACGGCGCC TGCTACACCA GCAAGCGCTG CGGCACTCAG
241 GCCGGCGGCA AGACATGCCC TAACAACCAC TGCTGCACCC AGTGGGGTTA CTGCGGCTTC
301 GGCGCCGAGT ACTGCGGCGC CGGCTGCCAG GGCGGCCCCT GCCGCGCCGA CATCAAGTGC
361 GGCAGCCAGG CCGGCGGCAA GCTTTGCCCC AACAACCTCT GCTGCAGCCA GTGGGGTTAC
421 TGCGGCCTCG GCTCCGAGTT CTGCGGCGAG GGCTGCCAGG GCGGTGCTTG CAGCACCGAC
481 AAGCCGTGCG GCAAGGCCGC CGGCGGCAAA GTTTGCACCA ACAACTACTG CTGCAGCAAG
541 TGGGGATCCT GTGGCATCGG CCCGGGCTAC TGCGGCGCAG GTTGCCAGAG CGGCGGCTGC
601 GACGGTGTCT TCGCCGAGGC CATCGCCGCC AACTCCACTC TTGTCGCAGA ATGATGATCT
661 TGCTAATGGC AGTATTATTG CAACGACGAA TAATCCGTGG CAGTTTTGTT GCCACGTACG
721 GTCTCCCTTC ACTTACTTTT AGCACTAGTC CTTAATAATT CTCCAGCCTT GCAATATGAC
781 GTGCAGGTTG CTACATGCAT GGACATATTG CAGTGAGAAG TACTGTGTGG CAATATAGGG
841 TGTACTATTG TTGCCACAAA TTTAGTTCTT TCTTGTTACG TACGTACAGT TGTCAGGATG
901 CATGCATCCC CGTTGTAATG TTGGAGTACT CCATGATTTC GTTGCAATAT ATATATTGCC
961 ATGAGTCTAA AG
```

FIG. 2

```
  1 GGAAGAGTTA TGAATATATT TATAGTTGTT TTATTATGTT TAACAGGTGT TGCAATTGCT
 61 GAGCAATGTG GTCGGCAAGC AGGTGGCAAG CTCTGCCCCA ATAACCTATG TTGTAGCCAG
121 TGGGGGTGGT GTGGCTCCAC TGATGAATAT TGTTCACCTG ATCATAACTG CCAAAGCAAT
181 TGCAAAGACA GCGGCGAAGG TGTTGGTGGT GGAAGTGCTT CCAACGTTCT TGCGACGTAC
241 CATTTGTATA ATTCACAGGA TCATGGATGG GACTTGAATG CCGCAAGTGC ATATTGCTCT
301 ACATGGGATG CTAACAAGCC ATATTCATGG CGGAGCAAGT ATGGCTGGAC TGCATTCTGC
361 GGTCCCGTCG GAGCACACGG CCAATCCTCC TGTGGAAAGT GCTTGAGTGT GACAAATACA
421 GGGACTGGAG CTAAAACGAC AGTGAGGATT GTGGATCAGT GTAGTAATGG AGGACTAGAT
481 TTGGACGTGA ATGTTTTCCG TCAACTGGAC ACAGATGGGA AAGGATATGA ACGAGGTCAT
541 ATTACAGTGA ACTACCAATT TGTTGATTGT GGAGATTCCT TCAATCCTCT ATTCTCCGTT
601 ATGAAATCAT CAGTAATTAA TTAATAACAT TGGATTGGAT GTATGTTTAA GTCCAATCGT
661 AGTAACTAAG CTTCTCAAGC AATAAGCAAC AACAAGGCCA ATTAATACTT CGTTGGCCAC
721 TATAAGAACT TGTGAAATGT TATGAGTTGT TGAAAGAGTT TGTTGTTGGA AATAATGGCA
781 TTTGAGCCAG CTCTGTAAGG TATTGGTGAA GATTATTGGG AAGATCGGCT ATCTCTTTAG
841 TGAGATATCC ATTGGTTTTC CCTTCCTCCT TCCTAAGTTG GGTGTATTTG AGTTACGATT
901 GTGTGTATTT GAGTTACGAT TGTGAGTTCA AGGTTGAGTG GCTTGTTATG AGTGAAAAAA
961 ATATTTAATG TTTATATTTT TTTTTATAT AATAAAAGTT TTGTTTGC
```

FIG. 3

```
   1 AATCATAGTA AGAAAGAAAA GATGATGATG AGGTTTTTAT CTGCCGTAGT GATCATGTCC
  61 TCCGCTATGG CGGTGGGTCT AGTGTCGGCA CAGAGGTGCG GAAGCCAAGG CGGCGGGGGT
 121 ACGTGTCCCG CCTTGTGGTG CTGCAGCATC TGGGGCTGGT GCGGCGACTC GGAGCCCTAC
 181 TGCGGCCGCA CCTGCGAGAA CAAGTGCTGG AGCGGCGAGC GGTCGGACCA CCGCTGCGGC
 241 GCCGCTGTAG GAAACCCTCC GTGCGGCCAG GACCGGTGCT GCAGCGTCCA CGGGTGGTGC
 301 GGTGGCGGCA ACGACTACTG CTCCGGGAGC AAATGCCAGT ACCGCTGCTC CTCCTCCGTC
 361 CGTGGACCCC GCGTCGCTCT CAGCGGCAAT TCCACCGCCA ACTCCATCGG CAACGTCGTC
 421 GTCACCGAGC CGCTGTTCGA CCAGATGTTC TCCCACCGCA AGGACTGTCC GAGCCAGGGC
 481 TTCTACAGCT ACCACTCCTT CCTCGTAGCC GCCGAGTCCT TCCCAGCTTT CGGGACCATC
 541 GGAGATGTTG CGACACGCAA GAGAGAGGTC GCAGCGTTCC TCGCCCATAT CTCCCAAGCA
 601 ACATCAGGGG AAAGGTCTGA CGTGGAAAAC CCTCATGCAT GGGGGCTTTG TCATATCAAT
 661 ACAACTACTG TGACTGAGAA TGACTTCTGT ACCTCCTCCG ACTGGCCTTG CGCTGCCGGC
 721 AAAAAATACA GCCCTCGAGG ACCCATCCAG CTCACCCACA ACTTCAACTA CGGACTTGCC
 781 GGCCAAGCCA TTGGAGAGGA CCTGATTCAG AACCCTGACT TGGTAGAAAA GGATCCAATC
 841 ATATCATTCA AGACGGCCTT GTGGTTCTGG ATGTCCCAGC ACGACAACAA ACCTTCATGC
 901 CATGACATTG TCCTCAATGC CAACTCCGCC GCGAACAGAA TCCCAAACAA AGGTGTGATC
 961 GGCAACATTA TTAGCCGCGC TTTTGGGCAC GACGACTTTG CCGTTAGATC TTCAAGCATC
1021 GGATTTTACA AGAGGTACTG CGACATGCTG GGAGTGAGCT ATGGACATGA CTTGAAGTAC
1081 TGGTTCGATA ACACTCCATC ATCGGAGTTC CAACGCATCC AAATGCGTGT TGCGGCGTAA
1141 AACAAGCTAG TCCTCCCCAA GTGGCTCTCT AGTAGTAAGA GTAGCTCTCT CATAGCGAGA
1201 GAGCGGCATG TTGAATCCCT GTTATGCTAT GTAATATTAT GTTACGCATG TATGTTAGAA
1261 ACATATATGT GTGATTTTCT AGCTCTTACG AGTTATAAAT AAAGTAGCCA CTTTCCT
```

FIG. 4

SEQUENCE LISTING

<160> NUMBER OF SEQ ID NOS: 3

<210> SEQ ID NO 1
<211> LENGTH: 972
<212> TYPE: DNA
<213> ORGANISM: Hordeum vulgare

<400> SEQUENCE: 1

| | | | | | | |
|---|---|---|---|---|---|---|
| cagaaaacaa | gaaggatgaa | gatgatgagc | accagggccc | tcgctctcgg | cgcggccgcc | 60 |
| gtcctcgcct | tcgcggcggc | gaccgcgcac | gcccagaggt | gcggcgagca | ggccagcaac | 120 |
| atggagtgcc | ccaacaacct | ctgctgcagc | cagtacgggt | actacggcat | gggcggcgac | 180 |
| tactgcggca | agggctgcca | gaacggcgcc | tgctacacca | gcaagcgctg | cggcactcag | 240 |
| gccggcggca | agacatgccc | taacaaccac | tgctgcaccc | agtggggtta | ctgcggcttc | 300 |
| ggcgccgagt | actgcggcgc | cggctgccag | ggcggcccct | gccgcgccga | catcaagtgc | 360 |
| ggcagccagg | ccggcggcaa | gctttgcccc | aacaacctct | gctgcagcca | gtggggttac | 420 |
| tgcggcctcg | gctccgagtt | ctgcggcgag | ggctgccagg | gcggtgcttg | cagcaccgac | 480 |
| aagccgtgcg | gcaaggccgc | cggcggcaaa | gtttgcacca | caactactg | ctgcagcaag | 540 |
| tggggatcct | gtggcatcgg | cccgggctac | tgcggcgcag | gttgccagag | cggcggctgc | 600 |
| gacggtgtct | tcgccgaggc | catcgccgcc | aactccactc | ttgtcgcaga | atgatgatct | 660 |
| tgctaatggc | agtattattg | caacgacgaa | taatccgtgg | cagttttgtt | gccacgtacg | 720 |
| gtctcccttc | acttactttt | agcactagtc | cttaataatt | ctccagcctt | gcaatatgac | 780 |
| gtgcaggttg | ctacatgcat | ggacatattg | cagtgagaag | tactgtgtgg | caatataggg | 840 |
| tgtactattg | ttgccacaaa | tttagttctt | tcttgttacg | tacgtacagt | tgtcaggatg | 900 |
| catgcatccc | cgttgtaatg | ttggagtact | ccatgatttc | gttgcaatat | atatattgcc | 960 |
| atgagtctaa | ag | | | | | 972 |

<210> SEQ ID NO 2
<211> LENGTH: 1008
<212> TYPE: DNA
<213> ORGANISM: Hevea brasiliensis

<400> SEQUENCE: 2

| | | | | | | |
|---|---|---|---|---|---|---|
| ggaagagtta | tgaatatatt | tatagttgtt | ttattatgtt | taacaggtgt | tgcaattgct | 60 |
| gagcaatgtg | gtcggcaagc | aggtggcaag | ctctgcccca | ataacctatg | ttgtagccag | 120 |
| tgggggtggt | gtggctccac | tgatgaatat | tgttcacctg | atcataactg | ccaaagcaat | 180 |
| tgcaaagaca | gcggcgaagg | tgttggtggt | ggaagtgctt | ccaacgttct | tgcgacgtac | 240 |
| catttgtata | attcacagga | tcatggatgg | gacttgaatg | ccgcaagtgc | atattgctct | 300 |
| acatgggatg | ctaacaagcc | atattcatgg | cggagcaagt | atggctggac | tgcattctgc | 360 |
| ggtcccgtcg | gagcacacgg | ccaatcctcc | tgtggaaagt | gcttgagtgt | gacaaataca | 420 |
| gggactggag | ctaaaacgac | agtgaggatt | gtggatcagt | gtagtaatgg | aggactagat | 480 |
| ttggacgtga | atgttttccg | tcaactggac | acagatggga | aaggatatga | acgaggtcat | 540 |
| attacagtga | actaccaatt | tgttgattgt | ggagattcct | tcaatcctct | attctccgtt | 600 |
| atgaaatcat | cagtaattaa | ttaataacat | tggattggat | gtatgtttaa | gtccaatcgt | 660 |
| agtaactaag | cttctcaagc | aataagcaac | aacaaggcca | attaatactt | cgttggccac | 720 |
| tataagaact | tgtgaaatgt | tatgagttgt | tgaaagagtt | tgttgttgga | ataatggca | 780 |

```
tttgagccag ctctgtaagg tattggtgaa gattattggg aagatcggct atctctttag      840
tgagatatcc attggttttc ccttcctcct tcctaagttg ggtgtatttg agttacgatt      900
gtgtgtattt gagttacgat tgtgagttca aggttgagtg gcttgttatg agtgaaaaaa      960
atatttaatg tttatatttt tttttttatat aataaaagtt ttgtttgc                 1008

<210> SEQ ID NO 3
<211> LENGTH: 1317
<212> TYPE: DNA
<213> ORGANISM: Urtica dioica

<400> SEQUENCE: 3
aatcatagta agaaagaaaa gatgatgatg aggtttttat ctgccgtagt gatcatgtcc       60
tccgctatgg cggtgggtct agtgtcggca cagaggtgcg gaagccaagg cggcgggggt      120
acgtgtcccg ccttgtggtg ctgcagcatc tggggctggt gcggcgactc ggagccctac      180
tgcggccgca cctgcgagaa caagtgctgg agcggcgagc ggtcggacca ccgctgcggc      240
gccgctgtag gaaaccctcc gtgcggccag gaccggtgct gcagcgtcca cgggtggtgc      300
ggtggcggca acgactactg ctccgggagc aaatgccagt accgctgctc ctcctccgtc      360
cgtggacccc gcgtcgctct cagcggcaat tccaccgcca actccatcgg caacgtcgtc      420
gtcaccgagc cgctgttcga ccagatgttc tcccaccgca aggactgtcc gagccagggc      480
ttctacagct accactcctt cctcgtagcc gccgagtcct tcccagcttt cgggaccatc      540
ggagatgttg cgacacgcaa gagagaggtc gcagcgttcc tcgcccatat ctcccaagca      600
acatcagggg aaaggtctga cgtggaaaac cctcatgcat ggggctttg tcatatcaat      660 acaactactg tgactgagaa tgacttctgt acctcctccg actggccttg cgctgccggc      720
aaaaaataca gccctcgagg acccatccag ctcacccaca acttcaacta cggacttgcc      780
ggccaagcca ttggagagga cctgattcag aaccctgact tggtagaaaa ggatccaatc      840
atatcattca agacggcctt gtggttctgg atgtcccagc acgacaacaa accttcatgc      900
catgacattg tcctcaatgc caactccgcc gcgaacagaa tcccaaacaa aggtgtgatc      960
ggcaacatta ttagccgcgc ttttgggcac gacgactttg ccgttagatc ttcaagcatc     1020 ggatttttaca agaggtactg cgacatgctg ggagtgagct atggacatga cttgaagtac     1080
tggttcgata acactccatc atcggagttc caacgcatcc aaatgcgtgt tgcggcgtaa     1140
aacaagctag tcctccccaa gtggctctct agtagtaaga gtagctctct catagcgaga     1200
gagcggcatg ttgaatccct gttatgctat gtaatattat gttacgcatg tatgttagaa     1260
acatatatgt gtgattttct agctcttacg agttataaat aaagtagcca ctttcct       1317
```

COTTON CELLS, PLANTS, AND SEEDS GENETICALLY ENGINEERED TO EXPRESS INSECTICIDAL AND FUNGICIDAL CHITIN BINDING PROTEINS (LECTINS)

CROSS-REFERENCE TO A RELATED APPLICATION

This application claims the benefit of provisional application Serial No. 60/087,219; filed May 29, 1998, which is hereby incorporated by reference in its entirety.

FIELD OF THE INVENTION

The present invention is directed to chimeric genes that express in cotton cells, plants and seeds, and encode insecticides and fungicides having substantially the insect toxicity and fungal toxicity of barley, nettle, and hevein lectins.

BACKGROUND OF THE INVENTION

Chitin-binding proteins (lectins) are present in a wide range of plant species, including both monocots and dicots, even though these plants contain no chitin. They are believed to be defense-related, and many exhibit insecticidal and/or anti-fungal activities (Murdock et. al., 1990; Lerner, D. R. and Raikhel, N. V., 1992). Lectins exhibit specific carbohydrate-binding properties. Lectins are presumably defense-related proteins in plants that exert their effect by binding to N-acetylglucosamine in susceptible pest species (Schroeder, M. R. and Raikhel, N. V. 1992).

In purified form, barley, nettle, and hevein lectins have shown insecticidal and fungicidal activity against certain species of pests which are known to attack cotton (for example, Heliothis and Fusarium). Various methods are available to utilize lectins to control such pests, but all require providing these proteins sufficiently pure and in sufficient quantity to effect control of the target insect or pathogen. Even when available in sufficient purity or quantity, they must be applied to the crop in such a way so as to effectively reach the target species. Furthermore, because they are proteins, if topically applied to crops they are subject to light and protease inactivation before they can exert their controlling effect. Root associated pathogens are not readily treated with such preparations. Hence, lectins have not been available for use in controlling many serious pests of cotton, even though they might be effective were they available in pure enough and high enough concentrations.

By taking advantage of genetic engineering, a gene responsible for the production of a useful polypeptide can be transferred from a donor cell, in which the gene naturally occurs, to a host cell, in which the gene does not naturally occur; Cohen and Boyer, U.S. Pat. Nos. 4,237,224 and 4,468,464. There are, in fact, few inherent limits to such transfers. Genes can be transferred between viruses, bacteria, plants, and animals. In some cases, the transferred gene is functional, or can be made to be functional, in the host cell. When the host cell is a plant cell, whole plants can sometimes be regenerated from the cell.

Genes typically contain regions of DNA sequences including a promoter and a transcribed region. The transcribed region normally contains a 5' untranslated region, a coding sequence, and a 3' untranslated region.

The promoter contains the DNA sequence necessary for the initiation of transcription, during which the transcribed region is converted into mRNA. In eukaryotic cells, the promoter is believed to include a region recognized by RNA polymerase and a region which positions the RNA polymerase on the DNA for the initiation of transcription. This latter region, which is referred to as the TATA box, usually occurs about 30 nucleotides upstream from the site of transcription initiation.

Following the promoter region is a sequence that is transcribed into mRNA but is not translated into polypeptide. This sequence constitutes the so-called 5' untranslated region and is believed to contain sequences that are responsible for the initiation of translation, such as a ribosome binding site.

The coding region is the sequence that is just downstream from the 5' untranslated region in the DNA or the corresponding RNA. It is the coding region that is translated into polypeptides in accordance with the genetic code. *Bacillus thuringiensis*, for example, has a gene with a coding sequence that translates into the amino acid sequence of an insecticidal crystal protein.

The coding region is followed by a sequence that is transcribed into mRNA, but is not translated into polypeptide. This sequence is called the 3' untranslated region and is believed to contain a signal that leads to the termination of transcription and, in eukaryotic mRNA, a signal that causes polyadenylation of the transcribed mRNA strand. Polyadenylation of the mRNA is believed to have processing and transportation functions.

Natural genes can be transferred in their entirety from a donor cell to a host cell. It is often preferable, however, to construct a gene containing the desired coding region with a promoter and, optionally, 5' and 3' untranslated regions that do not, in nature, exist in the same gene as the coding region. Such constructs are known as chimeric genes.

Barley lectin is a vacuolar protein synthesized with an amino-terminal signal sequence for entering the secretory pathway and a carboxyl-terminal propeptide necessary for proper targeting to the vacuole (Bednarek, S. Y., and Raikhel, N. V., 1991). The glycosylated carboxyl-terminal propeptide (CTPP) is removed before or concomitant with the deposition of the mature, active protein in vacuoles (Bednarek, et al., 1990). Mature barley lectin is a dimeric protein composed of two identical 18-kilodalton polypeptides (Wilkins, T. A., Bednarek, S. Y. and Raikhel, S. V., 1990). The nucleotide sequence and deduced amino acid sequence of the barley lectin coding region (barley lectin cDNA clone BLc3) has been reported (see Lemer and Raikhel, 1989; and U.S. Pat. No. 5,276,269, incorporated herein by reference). A chimeric gene construct was created by fusing the BLc3 coding region to the CaMV 35S promoter, and transferring the chimeric gene construct into tobacco plants via *Agrobacterium tumefaciens* mediated transformation (U.S. Pat. No. 5,276,269). Plants were reported to exhibit insecticidal and fungicidal properties.

A full length cDNA clone (HEV1) encoding *Hevea brasiliensis* lectin was isolated from a *H. brasiliensis* latex cDNA library, sequenced, and characterized (see Broekaert et al., 1990; Lee et al., 1991; and U.S. Pat. No. 5,187,262, incorporated herein by reference). Briefly, HEV1 is 1018 nucleotides long and includes an open reading frame of 204 amino acids. The deduced amino acid sequence contains a putative signal sequence of 17 amino acid residues followed by a 187 amino acid polypeptide. The amino-terminal region of 43 amino acids is identical to hevein and shows homology to several chitin-binding proteins and to the amino-termini of wound-induced genes in potato and poplar. Northern blots, using HEV1 cDNA as a probe, showed that the gene is induced by wounding and the plant hormones abscisic acid and ethylene. Accumulation of these transcripts was seen in leaves, stems, and latex, but not in roots. Chimeric gene constructs fusing the hevein coding region with heterologous promoters were not reported. However, tests with hevein protein showed antifungal activity against Trichoderma, Phycomyces, Botrytis, Septoria, Pyricularia, and Fusarium. The observed activities differed from those of wheat germ aglutinin (another lectin). Furthermore, hevein anti-fungal activity was found to be stable even after heating to 90° C., a condition under which certain chitinase activities are completely destroyed.

A full length cDNA encoding the nettle lectin (Urtica dioica agglutinin) has been cloned, sequenced, and characterized (Lerner and Raikhel, 1992). The protein is made up of 374 amino acids. 21 are a putative signal sequence and 86 amino acids encode the two chitin-binding domains of nettle lectin. These are fused to a 19 amino acid "spacer" domain and a 244 amino acid carboxyl extension with partial identity to a chitinase catalytic domain.

This gene represents another lectin heretofore unavailable as a source for resistance to important cotton insect and fungal pathogens.

The studies noted above underscore the complexity of the biochemistry of plant lectins. These are proteins which must be processed properly and transported into the proper subcellular compartment, usually a vacuole, where they are stored. In order to make use of these proteins in combating cotton pests, one viable approach is to generate chimeric gene constructs using various lectin genes and then transfer these into cotton using available transformation systems (see for example, Rangan et al., U.S. Pat. No. 5,244,802). Achieving an effective level of expression is not a given in heterologous systems. There would be no guarantee that the proteins would not have some unexpected toxic effect on the cotton plant itself, or that the proteins would exhibit the predicted pattern of activity. Furthermore, as noted above, some target pests attack plant tissues (for example, roots) in which some of these lectins are not normally expressed in the plants from which they come. Hence, a lectin which might have activity against a given pest in a feeding assay following topical application to plant tissue (see, for example, Cavalieri et. al., U.S. Pat. No. 5,407,454), may not exhibit that same activity when expressed in vivo.

Cavalieri et al. provides somewhat suggestive evidence that a broad range of plant lectins may provide a level of control against certain corn pests. Unfortunately, those studies were carried out using isolated lectin preparations for which essentially no biochemical characterization was provided. Some may even have been from commercial providers, where composition can vary from preparation to preparation. Hence, commercial providers include lot numbers with their products so that problems can be traced back on a lot by lot basis. Purity of the preparations was not discussed by Cavalieri, nor did they provide information on how they obtained their lectins or discuss the actual number of different lectins which may have been present in a given preparation. Any plant species may produce several different lectins, and protein preparations are readily contaminated with multiple protein species which may be present in trace amounts, but have a significant effect, positive or negative, on observed activity. Hence, the preparations tried may have actually been mixtures of lectins and even other proteins derived from the plants in question. No data were provided on the source of the lectin preparations used, on their purity, or hence on which of the lectin genes in a given plant the actual activity observed was based. Such preparations could have distinctly different insecticidal and fungicidal activities than a lectin provided in purified form from the expression in planta of a single lectin gene.

The best way to provide a protein in purified form, and therefore be certain of its activity against a given pest, is to isolate the gene and express the protein in an in vitro system. Since genes for most of the lectins cited in their study have still not been cloned as of this date, in vitro expression of single, purified lectins for analysis was not possible at the time Cavalieri et al. reported their data. Suggestive as their data is with respect to certain corn pests, Cavalieri et al. do not provide a single example of activity against a serious pest of cotton. Hence, their study is suggestive, but does not disclose a single lectin, in purified form, which one might use to control a significant pest of cotton.

Conversely, proteins which do not have activity in a feeding assay following topical application to plant tissues, may have activity when expressed in vivo. This could particularly be true in cotton, where plants normally express a compound called gossypol which is known to suppress feeding of certain insect pests. Thus, there could be synergistic effects between gossypol and lectins in such a way so as to enhance the insecticidal activity of a given lectin against important cotton pests. Alternatively, gossypol expression could suppress feeding just enough so that the target insect might never consume a potentially lethal amount of lectin. Hence, one could not know the insecticidal or fungicidal effect of a lectin gene transferred into cotton until such cotton cells, plants, and seeds were created.

Raikhel (U.S. Pat. No. 5,276,269) showed that a chimeric barley lectin gene under control of the CaMV 35S promoter could be transferred into tobacco plants to produce a single species lectin protein which was transported properly and thereby create a plant with new insecticidal and fungicidal properties. With the further availability of the hevein (Raikhel, U.S. Pat. No. 5,187,262) and nettle genes due to cloning (Lerner and Raikhel, 1992), it has now become possible to create cotton plants expressing in highly purified form each of these lectins and to test those cells, plants, and seeds for the presence of new insecticidal and fungicidal activities.

OBJECTS OF THE INVENTION

It is an object of the present invention to provide cotton cells, plants, and seeds expressing chimeric barley, nettle, and hevein lectin genes in amounts and under conditions which are sufficient to impart substantially the pesticidal properties such as insecticidal and fungicidal properties of barley, nettle, and hevein lectins to said cotton cells, plants, and seeds.

It is a further object of the present invention to provide a method for killing cotton insect pests and pathogens by feeding them cotton cells, plants, and seeds containing chimeric genes that express pesticidal (for example, insecticidal and fungicidal) amounts of a toxin having substantially the insect toxicities and fungal toxicities of barley, nettle, and hevein lectins.

It is an additional object of the present invention to provide the genes and other DNA segments within the cotton cells, plants, and seeds associated with the above methods.

SUMMARY OF THE INVENTION

These and other objects of the present invention have been achieved by providing chimeric genes capable of expressing in cotton cells, plants, and seeds a polypeptide having substantially the pesticidal toxicity (for example, the insect toxicity) and fungal toxicity of barley, nettle, and hevein lectins, in plant cells in culture and plant cells in living plants and seeds; as well as methods for producing a toxin having substantially the pesticidal properties (for example, the insect toxicity and fungal toxicity) of barley, hevein, and nettle lectins in cotton cells, plants, and seeds; and methods for killing cotton pests such as insects by feeding them cotton cells, plants, and seeds containing genes that express these toxins.

BRIEF DESCRIPTION OF THE DRAWINGS

FIG. 2 shows the nucleotide sequence of barley lectin cDNA clone BLc3 (Lerner and Raikhel, 1989; Raikhel U.S. Pat. No. 5,276,269).

FIG. 3 shows the nucleotide sequence of the hevein cDNA clone "HEV1" (Broekaert et al., 1990; Raikhel U.S. Pat. No. 5,187,262, incorporated herein by reference).

FIG. 4 shows the nucleotide sequence of the nettle lectin cDNA clone MK209 (Urtica dioica agglutinin; Lerner, D. R. and Raikhel, N. V., 1992, incorporated herein by reference).

BRIEF DESCRIPTION OF THE SEQUENCES

Figure 1:
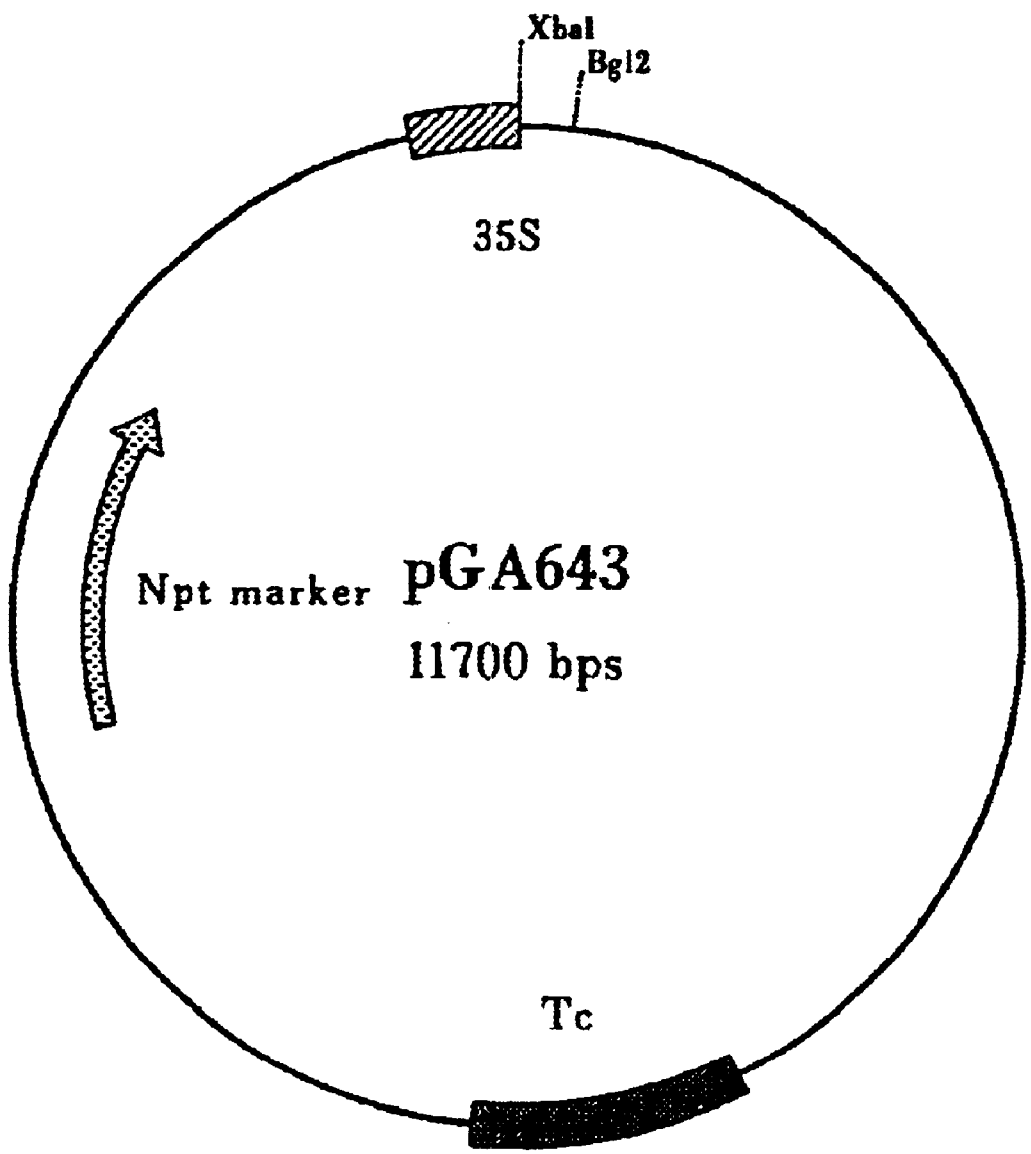
FIG. 1 illustrates the gene map and 35S promoter region of the binary plant expression vector pGA643 (described in An et al., 1988), which is useful for expression in plants of lectin genes (Wilkins et al., 1990; Raikhel U.S. Pat. No. 5,276,269, incorporated herein by reference).

SEQ ID NO. 1 is the nucleotide sequence of barley lectin cDNA clone BLc3 shown in FIG. 2.

SEQ ID NO. 2 is the nucleotide sequence of the hevein cDNA clone "HEV1" shown in FIG. 3; and SEQ ID NO. 3 is the nucleotide sequence of the nettle lectin cDNA clone MK209 shown in FIG. 4.

The present invention is directed to a chimeric gene that expresses in cotton cells, plants, and seeds, and encodes pesticides such as insecticides and fungicides having substantially the insect toxicity and fungal toxicity of barley, nettle, and hevein lectins.

The cotton plant cells contemplated include cells from any and all cotton plants into which foreign DNA can be introduced, replicated, and expressed. Some suitable examples of cotton plant species include *Gossypium hirsutum*, *Gossypium arboreum*, and *Gossypium barbadense*.

The term "plant cell" refers to any cell derived from a cotton plant. Some examples of cells encompassed by the present invention include differentiated cells that are part of a living plant; undifferentiated cells in culture; the cells of undifferentiated tissue such as callus or tumors; seeds; embryos; propagules; and pollen.

The chimeric gene of this invention contains a promoter region that functions efficiently in cotton plants and a coding region that codes for the barley lectin encoded in pBLc3, the hevein lectin encoded in the cDNA clone HEV1, and/or the nettle lectin encoded in the cDNA clone MK209. The coding sequence of the chimeric gene is not known to be associated with the promoter in natural genes.

The 5' and/or 3' untranslated regions may, independently, be associated in nature with either the promoter or the coding region, or with neither the promoter or the coding region. Preferably, either the 5' or the 3' untranslated region is associated with the promoter in natural genes, and most preferably both the 5' and 3' regions are associated with the promoter in natural genes.

One could not predict, based on the state of the art at the time this invention was made, that a chimeric barley, hevein, or lectin gene could be functionally introduced into cotton cells. It was even less predictable that such cells would express such lectins at sufficient levels to impart pesticidal (for example, insecticidal or fungicidal) properties to the cells.

In order to be considered pesticidal (for example, insecticidal or fungicidal), the plant cells must contain an insecticidal or fungicidal amount of lectin having substantially the insecticidal and fungicidal activity of purified lectin from barley, rubber, or nettle. Having "substantially the insecticidal and fungicidal activity of purified lectin" means exhibiting activity against substantially the same range of insects or fungi as does the corresponding lectin purified from its native host. An insecticidal or fungicidal amount is an amount which, when present in plant cells, kills insects or fungi or at least significantly inhibits a function necessary for growth, such as feeding. Such inhibition is that which can be measured as statistically significant when compared with a control. Accordingly, the plant cells, plants, or seeds of the present invention are able to withstand attacks by cotton pests such as insects, nematodes, or fungi without, or with less, application of purified barley lectin, hevein, nettle lectin, or other insecticides or fungicides when compared with plant cells, plants, or seeds that do not contain a gene producing barley lectin, hevein, or nettle lectin.

Following are examples which exemplify certain embodiments of the subject invention. These examples are illustrative and should not be construed as limiting the subject invention in any manner.

EXAMPLE 1

The Genes

Three different chimeric plant lectin genes (barley, hevein, and nettle), were evaluated in this study. Each comprised a cDNA for a given specific lectin driven by a promoter active in cotton. For convenience, the CaMV 35S promoter was used, but any promoter proven to be active in cotton, such as the *A. tumefaciens* T-DNA promoters, *A. rhizogenes* T-DNA promoters, or the cotton chlorophyll A/B binding protein gene promoter (Anderson, et al., 1993) would be useful. This list is exemplary, but not intended to be all inclusive. One skilled in the art will recognize other useful promoters which can be used to express barley, hevein, and nettle lectins in appropriate cotton cells, plants, and seeds to control problematic cotton pests such as insects and fungi.

An expression cassette comprising the coding region for barley lectin operably linked to the CaMV 35S promoter was created by ligating the pBLc3 cDNA sequence (FIG. 2) into the plant cloning vector pGA643 (FIG. 1; An et al., 1988) as described in Raikhel, U.S. Pat. No. 5,276,269 and incorporated herein by reference, taking advantage of the XbaI restriction endonuclease sites in pBLc3 and pGA643. Transformation was into the *E. coli* strain DH5α. Proper orientation of the coding region of the insert relative to the promoter region was confirmed by restriction endonuclease mapping and DNA sequence analysis. The clone comprising the coding region barley lectin cDNA pBLc3 in pGA643 can be obtained from Dr. N. Raikhel, MSU-DOE Plant Research Laboratory, Michigan State University, East Lansing, Mich., 48824.

An expression cassette comprising the coding region for hevein (*Hevea brasiliensis aglutinin*) operably linked to the CaMV 35S promoter was created by ligating the hevein cDNA sequence HEV1 (FIG. 3; Broekaert et al., 1990; Raikhel, U.S. Pat. No. 5,187,262) into the plant cloning vector pGA643 (FIG. 1; An et al., 1988) taking advantage of the XbaI and BglII restriction endonucleases which release the insert from HEV1 and cleave within the polylinker region of pGA643. Transformation was into the *E. coli* strain DH5α. Proper orientation of the coding region of the insert relative to the promoter region was confirmed by restriction endonuclease mapping and DNA sequence analysis. The clone comprising the HEV1 cDNA inserted into pGA643 can be obtained from Dr. N. Raikhel, MSU-DOE Plant Research Laboratory, Michigan State University, East Lansing, Mich., 48824.

An expression cassette comprising the coding region for nettle lectin operably linked to the CaMV 35S promoter was created by ligating the nettle cDNA sequence (FIG. 4) into the plant cloning vector pGA643 (FIG. 1; An et al., 1988). This was accomplished by releasing the insert from the nettle cDNA clone MK209 with XbaI and ligating this fragment into the XbaI restriction endonuclease site within the polylinker region of pGA643. Transformation was into the *E. coli* strain DH5α. Proper orientation of the coding region of the insert relative to the promoter region was confirmed by restriction endonuclease mapping and DNA sequence analysis. The nettle cDNA clone MK209 and the clone comprising the nettle coding region inserted into pGA643 can be obtained from Dr. N. Raikhel, MSU-DOE Plant Research Laboratory, Michigan State University, East Lansing, Mich., 48824.

All three binary vector constructs were mobilized from the *E. coli* strain DIH5α into *A. tumefaciens* LBA4404 by triparental mating (Hooykaas, P. J. J., 1988) using the *E. coli* strain HB101 harboring the wide-host range mobilizing plasmid pRK2013 (Clonetech, Palo Alto, Calif.). Transconjugates were selected on minimal nutrient plates (An et al., 1988) containing kanamycin (5 μg/ml) and tetracycline (12.5 μg/ml).

Cotton Transformation With Chimeric Lectin Genes

EXAMPLE 2

Cotten Regeneration

The establishment and maintenance of cotton embryogenic suspension cultures was as described in Rangan et al. (U.S. Pat. No. 5,244,802; incorporated herein by reference), as further modified in Rajasekaran et al., 1996 (incorporated by reference). For convenience, the cotton line B1654 was used. Many other upland or Pima cotton varieties will work equally well, and those skilled in the art would make their variety selection on the basis of the needs of their program.

Seeds were surface sterilized by first treating with 70% ethanol for 3 min, followed by a 20 min treatment with a 20% CLOROX solution (1% available chlorine) containing 0.01% of the surfactant TWEEN-20. Seedlings were grown under 16 h light (40–60 μE m$^{-2}$ s$^{-1}$) and 8 h dark at 26±2° C. on agar-solidified (TC Agar, Hazleton Biologics, Lenexa, Kans.) White's medium (Singh and Krikorian, 1981) containing 1 mg/l kinetin. Embryogenic callus cultures were first established from seedling explants according to the procedures of Rangan (U.S. Pat. No. 5,244,802). Briefly, cotyledon and hypocotyl explants from 7- to 10-day old seedlings were placed on a callus induction medium (MS, Murashige and Skoog, 1962) supplemented with 0.4 mg/l thiamine HCl, 30 g/l glucose, 2.0 mg/l α-naphthaleneacetic acid (NAA), 1.0 mg/l kinetin, 100 mg/l myo-inositol and 0.8% (w/v) agar. The cultures were incubated at 27±2° C. under conditions of 16h light and 8h dark, light intensity at 60 μE m$^{-2}$ s$^{-1}$, in an environmentally controlled incubator (Percival, Boone, Iowa). Callus formed on these explants within three to four weeks. Callus pieces were selectively subcultured to enrich for friable, yellowish-green callus every three to four weeks on the same medium, except the carbon source was sucrose (20 g/l) instead of glucose. Depending on the variety, embryogenic callus capable of forming small globular somatic embryos appeared one to four subcultures after initiation. Embryogenic callus was maintained and multiplied by routine subculture every three to four weeks on MS medium containing 100 mg/l myo-inositol, 20 g/l sucrose, 2.0 mg/l NAA and 0.8% (w/v) agar (maintenance medium).

Cell suspension cultures were initiated from finely dispersed embryogenic callus cultures in liquid maintenance medium agitated (120 rpm, 27±2° C.) on a gyratory shaker (New Brunswick G-10, Edison, N.J.).

The suspension cultures were enriched for small, isodiametric, densely cytoplasmic and highly embryogenic cells by periodically discarding free floating cells and large aggregates (≧840 μm) every week. Two days before use, these cultures were subcultured in 250 ml Erlenmeyer flasks containing 40 ml of maintenance medium. The cell suspension cultures used in our experiments were rapid growing embryogenic cells that exhibited a doubling of fresh weight in four to six days (the logarithmic phase of growth begins two days after subculture). All cell suspension cultures used for biolistic transformation experiments had a cumulative age of three to four months.

EXAMPLE 3

Biolistic Transformation of Embryogenic Cotton Cultures

The three plasmids (barley lectin coding region in pGA643; hevein coding region in pGA643; and nettle lectin coding region in pGA643) were used to coat 1.0 μM gold particles, and then projected into embryogenic cotton suspension cell cultures using an improved helium-driven biolistic device (PDS 1000/He; BioRad). Briefly, 50 μl of a gold micro-carrier suspension (1μ gold particles) in water was used. In an 1.5 ml micro-centrifuge tube, under continuous vortexing, the following were added in order: 5 μl DNA (1 μg/μl), 50 μl of 2.5M CaCl$_2$ and 20 μl of 0.1M spermidine (free base, tissue culture grade). Vortexing was continued for 3 minutes, the micro-carriers were spun down at 10,000 rpm for 10 seconds, and as much of the supernatant was removed as possible. The micro-carriers were washed with 250 μl of 100% ethanol (HPLC or spectrophotometric grade) by vortexing briefly, followed by centrifugation and removal of the supernatant. The micro-carriers were resuspended in 60 μl of 100% ethanol. 7.5 μl of this DNA coated micro-carrier mix were used per macro-carrier disk.

The bombardments were performed using a membrane rupture pressure of 1550 psi and other device settings as described by Hamilton et al. (8). The cell suspensions established as described above, (<840 μm fraction), subcultured two days earlier, were vacuum-deposited as a thin layer onto moist filter paper (Whatman No. 1; 3.5 cm diameter) in sterile Petri dishes (5.5 cm diameter). One ml of suspension cells (1×10$^6$ cells)was transferred to each dish. A 400 mesh nylon screen was placed over the surface of the suspensions to serve as a baffle. The optimal bombardment conditions included the use of 10 MPa rupture disks, a distance between the stopping screen and the cell suspensions of 7.5 cm and a macro-carrier travel distance of 10 mm. During the bombardment, the vacuum in the sample chamber was 95 kPa. Bombardment of the cells was repeated three to five times at two-day intervals to maximize the transformation frequency.

Following particle bombardment, the cell suspension cultures were grown for a week without any selection in maintenance medium. The pGA643 binary vector carries a neomycin phosphotransferase II gene for selection of transformed cells (FIG. 1). Accordingly, cell suspensions were selected with the antibiotic G418 (10 µg/ml). Selection with the antibiotic G418 was applied by gradually increasing the concentration each week. Selection with G418 was initiated at 10 µg/ml and increased by 10 µg/ml increments at five to seven day intervals to achieve a final concentration of 50 µg/ml after three to four weeks. Alternatively, in some experiments, cells were directly exposed to only one high level of antibiotic (G418 at 50 µg/ml) at the beginning of the selection process. Independent transformation events arose as separated growing colonies in the presence of the selective agent. Each colony so arising was maintained separately and verified as a true transformant via NPTII ELISA (Firoozabady et al., 1987). Cotton plants are regenerated from embryogenic suspension cultures as described in Rangan, U.S. Pat. No. 5,244,802 (incorporated herein by reference).

EXAMPLE 4

Agrobacterium Transformation With Lectin Genes

The three binary vector plasmids (barley lectin coding region in pGA643; hevein coding region in pGA643; and nettle lectin coding region in pGA643) were mobilized into the binary *A. tumefaciens* host strain LBA4404 by triparental mating as previously described. Transformation of cotton primary explants can be accomplished by a number of approaches (Firoozabady et al., 1987; Umbeck et al., 1987; Rangan, U.S. Pat. No. 5,244,802). For convenience, the method of Rangan, U.S. Pat. No. 5,244,802, as modified by Rajasekaran et al., 1996, is briefly described.

Agrobacterium cultures for transformation experiments were initiated in 50 ml of YEB liquid medium using frozen glycerol stocks (500 µl) as inoculum. These cultures were grown overnight for about 18 h at 26±2° C. on a gyratory shaker. The optical density (A600) values were adjusted to 0.6–0.8 in liquid MS medium prior to use.

Cotyledon (1 cm²) explants for Agrobacterium transformations are prepared from 5- to 7-day old seedlings. The explants are treated with an Agrobacterium suspension as prepared above for 15 to 30 min, blotted dry, and then plated on 12 cm diameter filter paper (Whatman No. 1) placed on freshly made, agar-solidified callus induction medium (Rangan U.S. Pat. No. 5,244,802) in 15 cm diameter Petri dishes containing 60 ml of medium. Cocultivation is carried out for 48 h in a Percival incubator maintained at 26±2° C., 16 h light, 60–90 µE m$^{-2}$s$^{-1}$. Following cocultivation, the explants are thoroughly washed in MS liquid medium containing 200 mg/l cefotaxime (Cal-Biochem) and 200 mg/l carbenicillin (Sigma), blotted dry, and placed on freshly prepared callus induction medium containing the antibiotic G418 (10 mg/l; Gibco BRL, Life Technologies, Gaithersburg, Md.) as the selection agent and the same concentrations of cefotaxime and carbenicillin as above to control bacterial growth. Cotyledon segments are plated at seven per Petri dish (9 cm diameter) containing 25 ml callus induction medium. After the first subculture the explants are transferred to freshly made callus induction medium to encourage more callus production in the presence of selection pressure. Transformed (antibiotic resistant) callus develops 3–8 weeks after transformation. Individual callus colonies are subcultured separately to maintain identity of separate integration events. NPT II ELISAs are carried out according to the procedures of Firoozabady et al., 1987 to confirm that antibiotic resistant callus colonies are transformed. Transformed colonies are regenerated to plants as described (Rangan, et al., U.S. Pat. No. 5,244,802)

Results

EXAMPLE 5

Confirmation of Cotton Transformation With Lectin Genes

Cotton cell lines (embryogenic colonies) transformed with barley, nettle, or hevein lectin genes in pGA643 were maintained as independent colonies in culture and confirmed to be transformed by NPTII ELISA as described above. To verify the co-transformation of the appropriate lectin gene along with the selectable marker in the transformation system employed, several NPTII ELISA positive colonies transformed with BLc3 were assayed using double-bind ELISA in methods similar in principle to those of Raikhel et al., 1984, but modified to be more suitable for transformed cotton cells.

Wheat germ agglutinin antibody, which is available commercially, will cross react with barley lectin (Wilkins et al., 1990) and hence can be used in detecting expression of BLc3 protein in transformed cotton cells using WGA ELISA. It was observed in initial studies with transformed cotton cells that cotton extracts give a high background reading when in these WGA ELISA tests for transformation. The following protocol was developed which overcomes this background problem and enabled the confirmation of co-transfer of lectin genes along with the antibiotic marker gene using the methods in the present invention.

Rabbit anti-wheat germ aglutinin (6 mg/ml) and biotinylated rabbit anti WGA (3.5 mg/ml) were purchased from E.Y. Laboratories. Primary antibody solution (1 µg/ml) was prepared by diluting 1.8µl of rabbit anti-WGA stock with 11 ml carbonate binding buffer (Na$_2$CO$_3$ 1.59 g, NaHCO$_3$ 2.93 g, H$_2$O to 1L, pH 9.6) and kept on ice. 100 µl were applied to each well of a 96 well ELISA plate (Corning #25805-96), sealed and kept overnight at 4° C.

Pre-adsorbed antibody was then prepared as follows. Four grams of control (non-transformed) callus was homogenized in 6 ml of PBS Tween prepared from 50× concentrate (Agdia, Elckhart, Indiana) containing 1% PVP 40,000 and centrifuged at 8,000 rpm for 10' to pellet cell debris. 5.5 ml of the supernatant was mixed with 5.5 ml of PBS TWEEN containing 0.1% BSA and 4% PEG 8,000. To this was added 9.4 µl biotinylated rabbit anti-WGA (E.Y.Laboratories, 3.5 mg/ml) for a final antibody concentration of 3 µg/ml. This was then incubated on ice for 3 hours to preadsorb the antibody.

ELISA plates were removed from the overnight incubation and washed thoroughly (4×) with PBS TWEEN. A blocking step was performed by filling each well of the plate with 1% BSA in PBS without TWEEN. PBS without TWEEN is prepared by combining 5 ml of a 10% stock w/v of Bovine Serum Albumin (Fraction V, ICN Pharmaceuticals

81-066 in water) with 5 ml of PBS(NaCl 8.0g, $Na_2HPO_4 \cdot 2H_2O$ 1.44g, $KH_2PO_4$ 0.2g, KCl $H_2O$ to 1L, adjusted to pH 7.4). The plates were incubated at room temperature (22° C.–24° C.) for 1 hour and then washed 4× with PBS TWEEN.

Extracts from embryogenic cell lines transformed with BLc3 were prepared as follows. About 0.5g of callus was homogenized in 130 μl PBS Tween containing 1% PVP 40,000 in a 1.5ml micro-centrifuge tube, centrifuged at 10,000 rpm to pellet cell debris, and held on ice. 100 μl of the supernatant was added to each well of the ELISA plates following the 1 hr blocking, washing step noted above. Plates were incubated for 3 hours at room temperature and washed 4× with PBS TWEEN. 100 μl of pre-adsorbed, biotinylated antibody were then added to each well of the plate, the plates were incubated overnight at 4° C., and washed 4× with PBS TWEEN.

Eleven ml of a 1:3000 dilution of streptavidin/alkaline phosphatase conjugate (from 5' to 3' ) was prepared in PBS (no TWEEN) containing 1% BSA. 100 μl were applied to each well of the ELISA plates and the plates were incubated for 1 hour at room temperature. The plates were washed 4× with PBS TWEEN. 200 μl of PNP (paranitrophenyl phosphate; Sigma 104 phosphate substrate #104-0) in 10% diethanolamine +0.5 mM $MgCl_2$, pH 9.8 (prepared immediately prior to use) was added per well and the color reaction was allowed to develop for 20 minutes at room temp. The reaction was stopped by the addition of 50 μl of 3N NaOH and the plates were read in a microplate reader at a wavelength of 410λ. Results of assays with several transformed embryogenic lines are presented in the following Table.

TABLE 1

Results of Immunoassays in WGA ELISA with cotton cells transformed with Blc3 in pGA643

| Sample # | Colony # | Lectin DNA | ELISA Result |
|---|---|---|---|
| 1 | control | none | − |
| 2 | control | none | − |
| 3 | control | none | − |
| 4 | control | none | − |
| 5 | control | none | − |
| 6 | 75 | BLC | − |
| 7 | 95 | BLC | − |
| 8 | 105 | BLC | − |
| 9 | 138 | BLC | − |
| 10 | 158 | BLC | − |
| 11 | 171 | BLC | − |
| 12 | 173 | BLC | − |
| 13 | 175 | BLC | − |
| 14 | 176 | BLC | ++ |
| 15 | 177 | BLC | + |
| 16 | 178 | BLC | +++ |
| 17 | 180 | BLC | − |
| 18 | 181 | BLC | − |
| 19 | 183 | BLC | − |
| 20 | 184 | BLC | + |
| 21 | 185 | BLC | − |
| 22 | 186 | BLC | + |
| 23 | 187 | BLC | − |
| 24 | 188 | BLC | +++ |
| 25 | 189 | BLC | − |
| 26 | 190 | BLC | ++ |
| 27 | 191 | BLC | − |
| 28 | 192 | BLC | − |
| 29 | 194 | BLC | + |
| 30 | 195 | BLC | +++ |
| 31 | 197 | BLC | +++ |
| 32 | 198 | BLC | + |
| 33 | 200 | BLC | +++ |

TABLE 1-continued

Results of Immunoassays in WGA ELISA with cotton cells transformed with Blc3 in pGA643

| Sample # | Colony # | Lectin DNA | ELISA Result |
|---|---|---|---|
| 35 | 203 | BLC | − |
| 36 | 205 | BLC | +++ |
| 37 | 207 | BLC | − |
| 38 | 209 | BLC | − |
| 39 | 211 | BLC | +++ |
| 40 | 216 | BLC | + |
| 41 | 25 μg/ml | WGA | +++ |

− = no signal detected.
+, ++, +++ indicates a signal detected and gives the relative intensity, with +++ being most intense.

The data in Table 1 confirm co-transfer of the lectin gene along with the NPTII selectable marker. Nearly 50% of the transformed embryogenic cell lines expressed sufficient lectin protein to be detectable in this assay. However, it is also evident that there was variability in the extent of the detectability of the BLc3 protein in these assays. This could be due to differences in the level of lectin protein expression in the separate transformation events represented by the different lines assayed.

EXAMPLE 6

Cotton Cells Transformed With BLc3 are Insecticidal

In order to confirm the insecticidal nature of cotton cells transformed with BLc3, feeding assays were preformed with larvae of the genus Heliothis. Heliothis species are economically important pests of cotton. Transformed embryogenic callus cultures which scored positive in both NPTII ELISA and WGA ELISA were selected for assay. Colonies were divided in two, with one half maintained in culture for regeneration to plants and one half used for the feeding assay. For the assay, >1 g of tissue was frozen in liquid nitrogen, lyophilized, and stored at –75° C. until used in the feeding assay.

Because corn ear worm is a significant pest of cotton, corn ear worm diet was used for this example. One skilled in the art would know to use an appropriate insect diet should one desire to assay transformed tissues for insecticidal activity against other insects. Insect diet was prepared as follows. 2.6 g agar was dissolved in 157 ml $H_2O$, boiled for 1 minute, and 40.6 g of corn ear worm diet (Bioserv Product #9394) was added and the mixture was stirred well. 1.5 ml of this mixture was added to each well of a 16 well insect feeding tray. To each well was then added 25 mg of lyophilized callus sample or control (non-transformed) sample as appropriate. Callus transformed with a truncated *Bacillus thuringiensis* (B.t.) crystalline endotoxin (CrylAb) gene ("pPHY3") was used as a positive control. This callus expresses Bt protein at a low level and is toxic to Heliothis larvae. Callus transformed with an NPTII gene ("pUC/NEO"), but without a lectin gene, served as the negative control.

*Heliothis virescens* larvae, a serious pest of cotton were used in this example. Eggs were allowed to hatch, and newly emerged larvae were applied, one per well of the insect feeding tray. After 6 days, larvae were weighed in order to determine extent of growth. The data are summarized in Table 2, which follows.

TABLE 2

| Results of Growth of Heliothis larvae on diet supplemented with cotton tissue transformed with BLc3 | | | |
|---|---|---|---|
| Callus #. | WGA ELISA Result | Avg. Larval Wt. Increase (% of Control) | Comment |
| pUC/NEO | – | 100% | Transformed with NPTII gene only |
| BLC 194 | + | 97% | 11% of the suppression achieved with pPHY3. |
| BLC 178 | +++ | 90% | 37% of the suppression achieved with pPHY3. |
| BLC 195 | +++ | 89% | 40% of the suppression achieved with pPHY3. |
| pPHY3 | – | 73% | 27% suppression of growth of negative control |

BLC numbers correspond to sample numbers in Table 1. Eight Heliothis larvae were tested for each callus test sample prepared as described in the text. The % growth weight increases shown are the average for the eight larvae after 6 days of feeding on the indicated test sample mix. The negative control sample was prepared using callus transformed with the NPTII marker alone (no lectin gene). The positive control was from tissue transformed with pPHY3.

The data in Table 2 show that cotton embryogenic callus transformed with BLc3 suppresses the growth of Heliothis larvae, and indeed killed some larvae, even with the relatively small amounts (25 mg) of lyophilized transformed callus mixed into the artificial diet in these studies.

EXAMPLE 7

Cotton Cells Transformed With HEVI (hevein) and MK209 (nettle lectin) are Insecticidal Corn ear worm diet supplemented with lyophilized callus was prepared as described in Example 6, except that the callus samples were derived from transformations carried out with HEVI and with MK209. Newly hatched larvae (1 per feeding test plate well) were placed on the test medium, incubated at room temperature, and then scored after 7 days. The data are summarized in the following Table 3.

TABLE 3

| Results of Growth of Heliothis larvae on diet supplemented with cotton tissue transformed with either HEVI (hevein) or MK209 (nettle lectin) | | |
|---|---|---|
| Callus #. | Avg. Larval Wt. Increase (% of Control) | Comment |
| pUC/NEO | 100% | Transformed with NPTII gene only |
| HEV 30 | 95% | 35% of suppression achieved with Bt. |
| MK209 34 | 86% | 108% of suppression achieved with Bt. |
| pPHY3 | 87% | 13% suppression of growth versus negative control |

The insect diet formulations employed in the present study included a very small percentage by weight of the test callus. Accordingly, the extent of insecticidal activity observed is to be deemed significant when one considers the relative activity versus the positive control. Although all lectin genes tested showed significant activity against Heliothis, the nettle lectin MK209 demonstrated the highest level of activity relative the B.t. endotoxin in this study.

One skilled in the art would know to use these methods to test cotton tissues transformed with the exemplified or other lectin genes for insecticidal activity against other insects and pests of economic importance in cotton production. Examples of such insects and pests include cutworms (Agrotis-spp., Paridroma spp., Euxoa spp., Feltia spp.), thrips (Franklinialla spp.), aphids (Aphis gossypii), bollworms (Heliothis spp., Pectinophora spp., Helicoverpa spp.), budworms (Heliothis spp.), plant bugs (Lygus spp., Euschistus spp.), boll weevil (Anthonomus grandis), armyworms (Spodoptera spp.), loopers (Alabama spp.), caterpillars (Estigmene spp.), cotton leaf perforator (Bacculatrix spp.), spider mites (Tetranychus spp.), whiteflies (Bemisia spp., Trialeurodes spp.), nematodes (Meloidogyne spp., Rotvlenchulus spp. Hoploaimus spp.), and fungal pathogens (Verticillium spp., Fusarium spp., Pvthium spp., Rhizoctonia spp., Thielaviopsis spp. Phytophthora spp.). In view of the foregoing examples, the skilled artisan will expect such tests with other lectins to be successful. Accordingly, it is clear that the invention is one encompassing embodiments other than those presented in the illustrative examples, and is to be construed by reference to the appended claims.

References

An G., Ebert, P. R., Mitra, A., and Ha, S. B (1988) *Binary vectors, Plant Mol. Biol. Manual* A3:1–19.

Anderson, D. M., Hudspeth, R. L., Hobbs, S. L., and Grula, J. W. (1993) *Plant Physiol.* 102:1047–1048.

Blake, M. S., Johnston, K. H., Russel-Jones, G. J., and Gotschlich, E. C. (1984) *Anal. Biochem.* 136:175–179.

Broekaert, W., Lee, H.-i., Kush, A., Chua, N.-H., and Raikhel, N. (1990) *Proc. Natl. Acad. Sci. U.S.A.* 87:7633–7637.

Firoozabady, E., DeBoer, D., Merlo, D., Halk, E. Amerson, L., Rashka, K., and E. Murray (1987) *Plant Mol. Biol.* 10: 105–116.

Hooykaas, P. J. J. (1988) *Plant Molec. Biol. Manual* A4:1–13.

Lee, Hyung-il, Broekaert, W F., and Raikhel, N. V. (1991) *J. Biol. Chem.* 266:15944–15948.

Lerner, D. R., and Raikhel, N. V. (1989) *Plant Physiol.* 91:124–129.

Lerner, D. R., and Raikhel, N. V. (1992) *J. Biol. Chem.* 267:22694.

Murashige, T. and Skoog, F. (1962) *Physiol. Plant.* 15:4730497

Murdock et. al. (1990) *Phytochemistry* 29:85–89.

Raikhel, N. V., Mishkind, M. L., and Palevitz, B. A. (1984) *Planta* 162:55–61.

Rajasekaran, K. Grula, J. W., Hudspeth, R. L., Pofelis, S., and Anderson, D. M. (1996) *Molecular Breeding* 2:307–319.

Schroeder, M. R. and Raikhel, N. V. (1992) *Protein Expr. Purif.* 3:508–511.

Singh, M. and Krikorian, A. D. (1981) *Ann. Bot.* 47:133–139.

Umbeck, P., Johnson, G., Barton, K., and W. Swain (1987) *Bio/technology* 5:263–266.

Wilkins, T. A., Bednarek, S. Y., and Raikhel, N. V. (1990) *The Plant Cell* 2:301–313.

What is claimed is:

1. A plurality of cotton cells comprising a heterologous coding sequence encoding a pesticidal lectin, said coding sequence being expressed in said cells, whereby said cells are rendered pesticidal; wherein said lectin is a barley lectin.

2. A plurality of cotton cells comprising a heterologous coding sequence encoding a pesticidal lectin, said coding sequence being expressed in said cells, whereby said cells are rendered pesticidal; wherein said lectin is a nettle lectin.

3. A plurality of cotton cells comprising a heterologous coding sequence encoding a pesticidal lectin, said coding sequence being expressed in said cells, whereby said cells are rendered pesticidal; wherein said lectin is a hevein lectin.

4. A cotton plant, comprising a plurality of cotton cells comprising a heterologous coding sequence encoding a pesticidal lectin, said coding sequence being expressed in said cells, whereby said cells are rendered pesticidal; wherein said lectin is a barley lectin.

5. A cotton plant, comprising a plurality of cotton cells comprising a heterologous coding sequence encoding a pesticidal lectin, said coding sequence being expressed in said cells, whereby said cells are rendered pesticidal; wherein said lectin is a nettle lectin.

6. A cotton plant, comprising a plurality of cotton cells comprising a heterologous coding sequence encoding a pesticidal lectin, said coding sequence being expressed in said cells, whereby said cells are rendered pesticidal; wherein said lectin is a hevein lectin.

7. A seed of the cotton plant of claim 4, wherein said seed comprises the heterologous lectin-encoding sequence.

8. A seed of the cotton plant of claim 5, wherein said seed comprises the heterologous lectin-encoding sequence.

9. A seed of the cotton plant of claim 5, wherein said seed comprises the heterologous lectin-encoding sequence.

10. A method of producing a pesticidal lectin comprising the steps of:

obtaining a pesticidal lectin-encoding polynucleotide;

transforming cotton cells with said polynucleotide;

culturing said cells under conditions whereby transgenic cotton cells comprising said polynucleotide or a plant comprising said transgenic cells are produced; and verifying that said polynucleotide is expressed in said transgenic cells, whereby a pesticidal lectin is produced; wherein said lectin is a barley lectin.

11. A method of producing a pesticidal lectin comprising the steps of:

obtaining a pesticidal lectin-encoding polynucleotide;

transforming cotton cells with said polynucleotide;

culturing said cells under conditions whereby transgenic cotton cells comprising said polynucleotide or a plant comprising said transgenic cells are produced; and verifying that said polynucleotide is expressed in said transgenic cells, whereby a pesticidal lectin is produced; wherein said lectin is a nettle lectin.

12. A method of producing a pesticidal lectin comprising the steps of:

obtaining a pesticidal lectin-encoding polynucleotide;

transforming cotton cells with said polynucleotide;

culturing said cells under conditions whereby transgenic cotton cells comprising said polynucleotide or a plant comprising said transgenic cells are produced; and verifying that said polynucleotide is expressed in said transgenic cells, whereby a pesticidal lectin is produced; wherein said lectin is a hevein lectin.

13. A method of producing a pest-resistant cotton plant comprising the steps of:

obtaining a pesticidal lectin-encoding polynucleotide;

transforming cotton cells with said polynucleotide;

culturing said cells under conditions whereby a cotton plant is produced comprising transgenic cells which comprise said lectin-encoding polynucleotide; and verifying that said polynucleotide is expressed in said transgenic cells, whereby a pesticidal lectin is produced; wherein said lectin is a barley lectin.

14. A method of producing a pest-resistant cotton plant comprising the steps of:

obtaining a pesticidal lectin-encoding polynucleotide;

transforming cotton cells with said polynucleotide;

culturing said cells under conditions whereby a cotton plant is produced comprising transgenic cells which comprise said lectin-encoding polynucleotide; and verifying that said polynucleotide is expressed in said transgenic cells, whereby a pesticidal lectin is produced; wherein said lectin is a nettle lectin.

15. A method of producing a pest-resistant cotton plant comprising the steps of:

obtaining a pesticidal lectin-encoding polynucleotide;

transforming cotton cells with said polynucleotide;

culturing said cells under conditions whereby a cotton plant is produced comprising transgenic cells which comprise said lectin-encoding polynucleotide; and verifying that said polynucleotide is expressed in said transgenic cells, whereby a pesticidal lectin is produced: wherein said lectin is a hevein lectin.

16. The method of claim 13, further comprising the steps of growing said plant under conditions whereby cotton seed are produced;

harvesting at least one cotton seed from said plant; and producing descendant pest resistant cotton plants front said plant.

17. method of claim 14, further comprising the steps of growing said plant under conditions whereby cotton seed are produced;

harvesting at least one cotton seed from said plant; and producing descendant pest resistant cotton plants from said plant.

18. A method of claim 15 further comprising the steps of growing said plant under conditions whereby cotton seed are produced;

harvesting at least one cotton seed from said plant; and producing descendant pest resistant cotton plants from said plant.

19. A method of inhibiting a cotton pest comprising the steps of:

obtaining a pesticidal lectin-encoding polynucleotide;

transforming cotton cells with said polynucleotide;

culturing said cells under conditions whereby transgenic cotton cells comprising said polynucleotide or a plant comprising said transgenic cells are produced;

verifying that said polynucleotide is expressed in said transgenic cells, whereby a pesticidal lectin is produced; and allowing said transgenic cells to be contacted by a cotton pest; wherein said lectin is a barley lectin.

20. A method of inhibiting a cotton pest comprising the steps of:

obtaining a pesticidal lectin-encoding polynucleotide;

transforming cotton cells with said polynucleotide;

culturing said cells under conditions whereby transgenic cotton cells comprising said polynucleotide or a plant comprising said transgenic cells are produced;

verifying that said polynucleotide is expressed in said transgenic cells, whereby a pesticidal lectin is produced; and allowing said transgenic cells to be contacted by a cotton pest; wherein said lectin is a nettle lectin.

21. A method of inhibiting a cotton pest comprising the steps of:

obtaining a pesticidal lectin-encoding polynucleotide;

transforming cotton cells with said polynucleotide;

culturing said cells under conditions whereby transgenic cotton cells comprising said polynucleotide or a plant comprising said transgenic cells are produced;

verifying that said polynucleotide is expressed in said transgenic cells, whereby a pesticidal lectin is produced; and allowing said cells to be contacted by pest; wherein said lectin is a hevein lectin.

* * * * *

UNITED STATES PATENT AND TRADEMARK OFFICE
CERTIFICATE OF CORRECTION

PATENT NO. : 6,710,228 B1
DATED : March 23, 2004
INVENTOR(S) : Richard Lee Yenofsky et al.

It is certified that error appears in the above-identified patent and that said Letters Patent is hereby corrected as shown below:

Column 2,
Line 46, "(see Lemer and" should read -- (see Lerner and Raikhel,... --.

Column 4,
Line 37, "(Lemer and Reikhel, 1992)," should read -- (Lerner and Raikhel, --.

Column 7,
Line 32, "...DIH5α..." should read -- ...DH5α... --.
Line 44, "Cotten Regeneration" should read -- Cotton Regeneration --.

Column 11,
Line 2, "...KCI $H_2O$..." should read -- ...KCl 0.2g, $H_2O$... --.

Column 14,
Line 19, "Rotvlenchulus spp." should read -- Rotylenchulus spp. --.
Line 20, "Pvthium spp." should read -- Pythium spp. --.

Column 19,
Line 1, "...of claim 5," should read -- ...of claim 6," --.

Column 20,
Line 11, "17. method of claim 14," should read -- 17. The method of claim 14 --.
Line 62, "...allowing said cells to be contacted by pest;" should read -- allowing said cells to be contacted by a cotton pest; --.

Signed and Sealed this

Third Day of August, 2004

JON W. DUDAS
*Acting Director of the United States Patent and Trademark Office*